United States Patent
Scarlata et al.

(10) Patent No.: US 10,508,965 B2
(45) Date of Patent: Dec. 17, 2019

(54) SEALANT DETECTION APPARATUS, METHOD AND ASSEMBLY

(71) Applicant: Eaton Intelligent Power Limited, Dublin (IE)

(72) Inventors: Andrew F. Scarlata, West Monroe, NY (US); Jesse W. Taylor, Baldwinsville, NY (US); Benjamin A. Freer, Syracuse, NY (US); Adikaramge A. Jayawardena, Manlius, NY (US); Joseph M. Manahan, Manlius, NY (US)

(73) Assignee: Eaton Intelligent Power Limited, Dublin (IE)

( * ) Notice: Subject to any disclaimer, the term of this patent is extended or adjusted under 35 U.S.C. 154(b) by 222 days.

(21) Appl. No.: 15/624,945

(22) Filed: Jun. 16, 2017

(65) Prior Publication Data

US 2017/0363553 A1    Dec. 21, 2017

Related U.S. Application Data

(60) Provisional application No. 62/350,839, filed on Jun. 16, 2016.

(51) Int. Cl.

| | |
|---|---|
| *G01M 3/18* | (2006.01) |
| *G01N 25/54* | (2006.01) |
| *G01N 33/22* | (2006.01) |
| *G01N 33/00* | (2006.01) |
| *G01N 29/22* | (2006.01) |
| *G01M 3/24* | (2006.01) |
| *G01M 3/14* | (2006.01) |

(Continued)

(52) U.S. Cl.
CPC ............ *G01M 3/183* (2013.01); *G01M 3/143* (2013.01); *G01M 3/243* (2013.01); *G01N 25/54* (2013.01); *G01N 29/221* (2013.01); *G01N 29/223* (2013.01); *G01N 33/0057* (2013.01); *G01N 33/225* (2013.01); *B60R 16/0215* (2013.01); *G01R 27/18* (2013.01); *H02G 3/02* (2013.01); *H02G 3/0412* (2013.01); *H02G 3/06* (2013.01); *H02G 3/22* (2013.01); *H02G 15/013* (2013.01)

(58) Field of Classification Search
CPC ... G01N 29/221; G01N 29/223; G01M 3/183; G01M 3/243
See application file for complete search history.

(56) References Cited

U.S. PATENT DOCUMENTS

| | | | | |
|---|---|---|---|---|
| 4,216,349 A | * | 8/1980 | Wium | H01B 17/306 174/23 R |
| 2004/0227302 A1 | * | 11/2004 | Burdick | F16J 15/004 277/510 |
| 2017/0146492 A1 | * | 5/2017 | Luo | G01H 5/00 |

OTHER PUBLICATIONS

Article 500-516 of the National Electrical Code® with product recommendations for use in hazardous (classified) areas. https://www.crouse-hinds.de/download/1/crouse-hinds-codedigest2014.pdf (Jan. 2014).

* cited by examiner

*Primary Examiner* — Paul M. West
(74) *Attorney, Agent, or Firm* — Merchant & Gould P.C.

(57) ABSTRACT

Apparatus, assembly and method for investigating the integrity of a seal and sealant contained in a sealing fitting used in hazardous locations. The apparatus/assembly can include signal transmitters and signal receivers provided on a conduit system on either side of a sealing fitting. The apparatus/assembly can include probes placed on either side of a (Continued)

sealant within a sealing fitting, the probes placed in probe ports provided through the wall of the sealing fitting.

20 Claims, 6 Drawing Sheets

(51) Int. Cl.
*B60R 16/02* (2006.01)
*G01R 27/18* (2006.01)
*H02G 3/02* (2006.01)
*H02G 3/22* (2006.01)
*H02G 3/04* (2006.01)
*H02G 3/06* (2006.01)
*H02G 15/013* (2006.01)

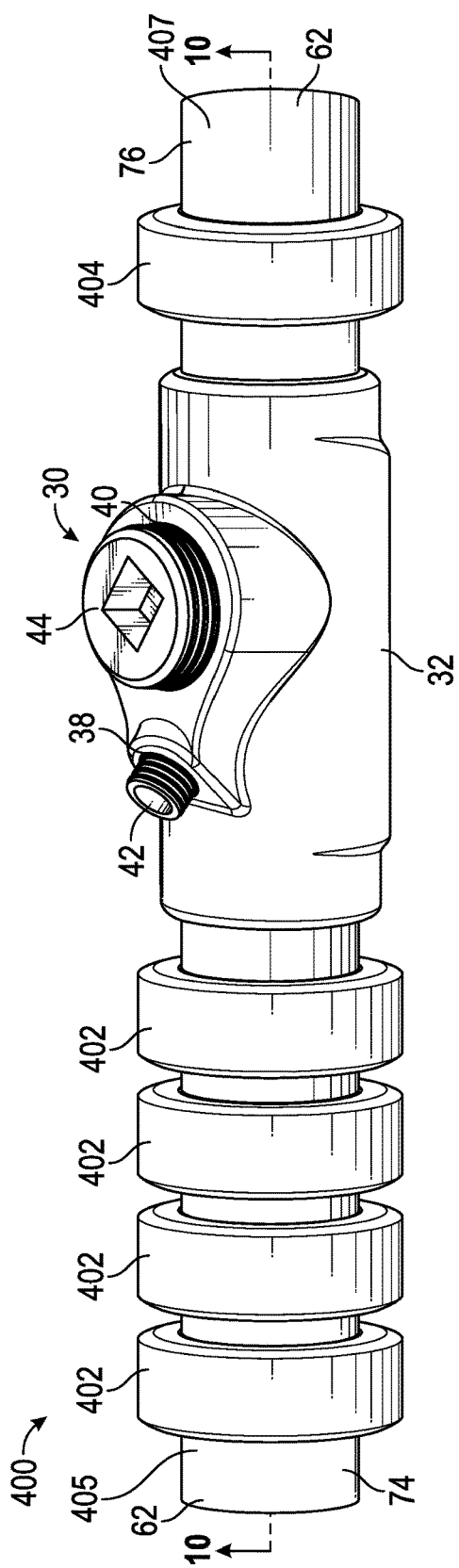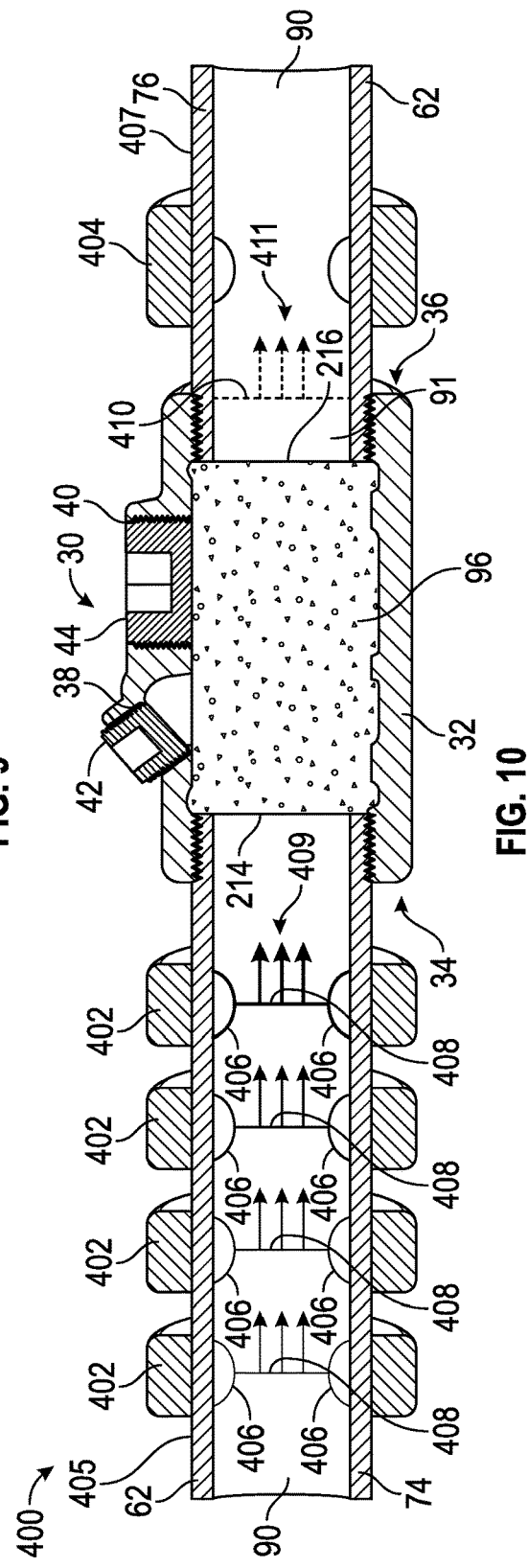
FIG. 9
FIG. 10

SEALANT DETECTION APPARATUS, METHOD AND ASSEMBLY

CROSS REFERENCE TO RELATED APPLICATIONS

This application claims the benefit of U.S. Provisional Patent Application No. 62/350,839, filed Jun. 16, 2016, which application is hereby incorporated by reference in its entirety.

BACKGROUND

Explosion proof enclosures are commonly used in hazardous locations in order to contain explosions that may occur within the enclosure and prevent sparks occurring within the enclosure from igniting vapors, gases, or other materials in the area surrounding the enclosure. Hazardous locations may include, for example, aircraft hangars, gasoline stations, paint finishing locations, agricultural areas, etc.

The National Electric Code (NEC®) defines classes and divisions of hazardous locations, as well as requirements for explosion proof enclosures used in such locations. For example, a Class I hazardous location or area is one in which flammable gases or vapors are/could become present in concentrations suitable to produce explosive and/or ignitable mixtures. A typical class I area is a petroleum processing facility, for example. Within Class I, a Division 1 area or location includes: one where the atmosphere of the area is expected to contain explosive mixtures of gases, vapors or liquids during normal working operations; one where ignitable concentrations frequently exist because of repair or maintenance operations; or one where there is release of ignitable concentrations of gases or vapors due to equipment breakdown, while at the same time causing electrical equipment failure. A Class I, Division 2 hazardous location includes: one where flammable liquids or gases are handled, but not expected to be in explosive concentrations, with the possibility of explosive concentrations resulting from an accidental rupture or other unexpected incident; one where ignitable gases or vapors are normally prevented from accumulating by positive mechanical ventilation, but could exist in ignitable quantities if there is a failure in the ventilation system; and areas adjacent to Class I, Division 1 locations where it is possible for ignitable concentrations of gas/vapors to enter the area due to lack of proper ventilation.

Explosion proof enclosures often have conduits leading to them. Such conduits may carry cable or wiring, for example, to power and/or control machinery inside the enclosure, such as a motor or a compressor.

The features of the conduit and how they connect to the explosion proof enclosure are highly regulated. For example the NEC provides that in Class I, Division 1 locations, all conduits generally must be rigid metal or steel IMC with at least five fully tapered threads tightly engaged in the enclosure. In some applications, conduits are fortified with one or more corrosion resistant coatings.

Conduit systems are generally not airtight, such that the type and concentration of gases outside the conduit can also be present inside the conduit. Thus, conduits are provided with seals to prevent explosions from spreading through conduit systems. Seals create a physical barrier that minimizes the passage of gases travelling through the conduit, and also limit the passage of vapors between hazardous and non-hazardous locations. Seals can also serve to prevent pressure piling, i.e., the buildup of pressure inside a conduit caused by precompression as the explosion travels through the conduit.

Conduit system seals are usually provided in a sealing fitting. An example of an industry standard sealing fitting 30 is depicted in FIG. 2. The NEC provides that sealing fittings are required at each entrance to an enclosure housing an arcing or sparking device when used in a Class I, Division 1 and 2 hazardous locations, and at each entrance of two inch size or larger to an enclosure or fitting housing terminals, splices or taps when used in Class I, Division 1 hazardous locations. In these scenarios, the sealing fitting must be as close as practicable to the enclosure and in no case more than 18 inches from the enclosure. In addition, the NEC provides for installing sealing fittings in conduit systems when leaving Class I, Division 1 or 2 hazardous locations, and in cable systems when the cables either do not have a gas/vaportight continuous sheath or are capable of transmitting gases or vapors through the cable core when those cables leave Class I, Division 1 or 2 hazardous locations.

As mentioned above, typical conduit systems are not airtight. Therefore, changes in temperature or barometric pressure can cause a "breathing" effect in which air enters the conduit system or enclosure. Once air enters a conduit, for example, moisture in the air can condense. If the conduit runs non-horizontally, the condensed water can collect at the base of the conduit, potentially causing equipment shorts or grounds. In these situations, sealing fittings that include a drainage feature can be used to provide an explosion proof path for water to exit while still sealing the conduit.

The seals in sealing fittings are inspected to determine if the seal is compromised and should be reinforced or replaced. Typically, the inspection has to be performed visually through a port provided in the sealing fitting. Such inspection will often fail to reveal sealant imperfections or degradations occurring outside the small field of view (i.e., the sealant directly under the plug) available during a visual inspection, which would otherwise alert the technician to a potentially hazardous condition that should be remedied. In addition, seals in sealing fittings are often prepared by electricians, who may not have extensive training in how to properly and sufficiently introduce sealant to the sealing fitting.

There is a need to improve sealant inspection and verification in sealing fittings used in or near hazardous locations.

SUMMARY

One aspect of the present disclosure relates to a sealing fitting rated for use in a hazardous environment, the sealing fitting comprising a wall defining an interior space and having an inner surface and an outer surface, and including first and second ports through the wall into the interior space, the ports being disposed, respectively, beyond the proximal and distal extremes of a sealant disposed within the fitting, the sealant being configured to limit the passage of vapors between an explosion-proof enclosure and the atmosphere of a Class I hazardous location, wherein sealant inspection means are inserted into the first and second ports to inspect the integrity of the seal formed by the sealant.

Another aspect of the present disclosure relates to a method for inspecting sealant disposed in a sealing fitting rated for use in a hazardous environment, the sealing fitting comprising a wall defining an interior space and having an inner surface and an outer surface, the method including the steps of: providing a first port through the wall into the interior space on one of a proximal end and a distal end of a sealant disposed in the fitting; providing a second port though the wall into the interior space on the other of the proximal end and distal end of the sealant; inserting a probe in each of the first and second ports; receiving a signal sent from the first probe and received by the second probe; and evaluating an integrity of the seal/sealant based on the signal received by the second probe.

Another aspect of the present disclosure relates to an assembly for inspecting a seal in a conduit system for use in a hazardous environment, the conduit system comprising a sealing fitting having first and second ends, a sealant disposed in an interior space of the sealing fitting between the first and second ends, a first conduit connected to the first end, and a second conduit connected to the second end, the assembly comprising a signal transmitter disposed on the first conduit, and a signal receiver disposed on the second conduit, the signal receiver being configured to receive one or more signals transmitted by the signal transmitter through the sealant.

Another aspect of the present disclosure relates to a method for inspecting sealant disposed in a sealing fitting for use in a hazardous environment, the sealing fitting having first and second ends, a sealant disposed in an interior space of the fitting between the first and second ends, a first conduit connected to the first end, and a second conduit connected to the second end, the method comprising: providing a signal transmitter on the first conduit; providing a signal receiver on the second conduit, the signal receiver being configured to receive one or more signals transmitted by the signal transmitter through the sealant; transmitting a signal from the signal transmitter to the signal receiver through the sealant; and evaluating an integrity of the seal/sealant based on the signal received by the signal receiver.

Another aspect of the present disclosure relates to a sealing fitting rated for use in a hazardous environment, the sealing fitting comprising: a wall defining an interior space and having an inner surface and an outer surface, the wall being defined by a longitudinal axis, a first end, and a second end, the interior space comprising a sealant receiving portion, a first sealant dam receiving portion, and a second sealant dam receiving portion, the sealant receiving portion having a distal extreme and a proximal extreme, the first sealant dam receiving portion extending distally from the distal extreme of the sealant receiving portion, the second sealant dam receiving portion extending proximally from the proximal extreme of the sealant receiving portion; first screw threads at the first end for threadably securing a first conduit to the sealing fitting; second screw threads at the second end for threadably securing a second conduit to the sealing fitting; a pluggable first port for accessing the interior space, the pluggable first port being disposed in an outwardly projecting portion of the wall and aligned perpendicularly with the longitudinal axis; a pluggable second port for accessing the interior space, the pluggable second port being disposed in the outwardly projecting portion of the wall and aligned obliquely with the longitudinal axis; a first probe port, the first probe port comprising a first aperture through the wall from the outer surface to the inner surface, the first probe port being positioned between the first end and the pluggable first port and aligning with an axis that passes through the interior space of the sealing fitting between the first screw threads and the first sealant dam receiving portion; and a second probe port, the second probe port comprising a second aperture through the wall from the outer surface to the inner surface, the second probe port being positioned between the second end and the pluggable second port and aligning with an axis that passes through the interior space of the sealing fitting between the second screw threads and the second sealant dam receiving portion.

BRIEF DESCRIPTION OF THE DRAWINGS

FIG. 9 is an isometric view of an assembly in accordance with the present disclosure for inspecting sealant in the sealing fitting of FIG. 2 used in a Class I hazardous location.

FIG. 10 is a longitudinal cross-sectional view of the assembly of FIG. 9 along the line marked 10-10 in FIG. 9.

DETAILED DESCRIPTION

Figure 1:
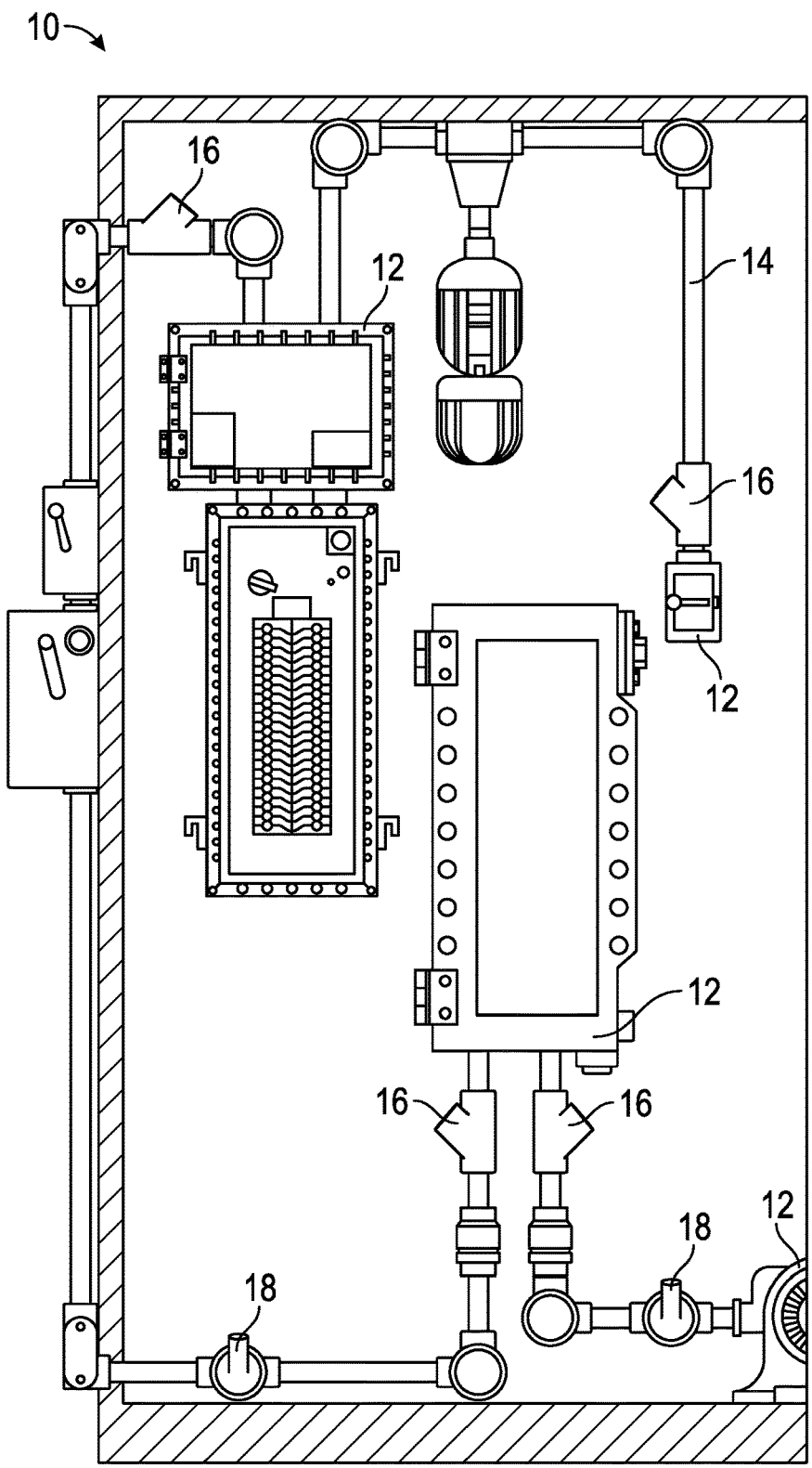
FIG. 1 is a schematic view of an example Class I, Division 1 hazardous location.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a schematic view of an example Class I, Division 1 hazardous location 10. The hazardous location 10 includes a plurality of explosion-proof enclosures 12 and a conduit system 14. The conduit system 14 includes a plurality of first sealing fittings 16 and second sealing fittings 18 in proximity to the explosion-proof enclosures 12. The first sealing fittings 16 (e.g., expanded fill sealing fittings) are used along horizontal and vertical conduits of the conduit system 14. The second sealing fittings 18 are used along conduits in the conduit system 14 that are oriented neither horizontally nor vertically. Both the first and second sealing fittings (16, 18), may be provided in a male configuration or a female configuration as appropriate for the conduit to which it couples.

Detailed descriptions of the disclosed apparatus and method are provided below with reference to female sealing fittings configured for use in a horizontal or vertical orientation in a conduit system. It should be appreciated, however, that the principles of these disclosures are readily applicable to other sealing fittings, e.g., male sealing fittings, sealing fittings configured for non-horizontal, non-vertical orientations, or specialized sealing fittings such as those configured to provide for water runoff away from the sealant and conduit system.

Figure 2:
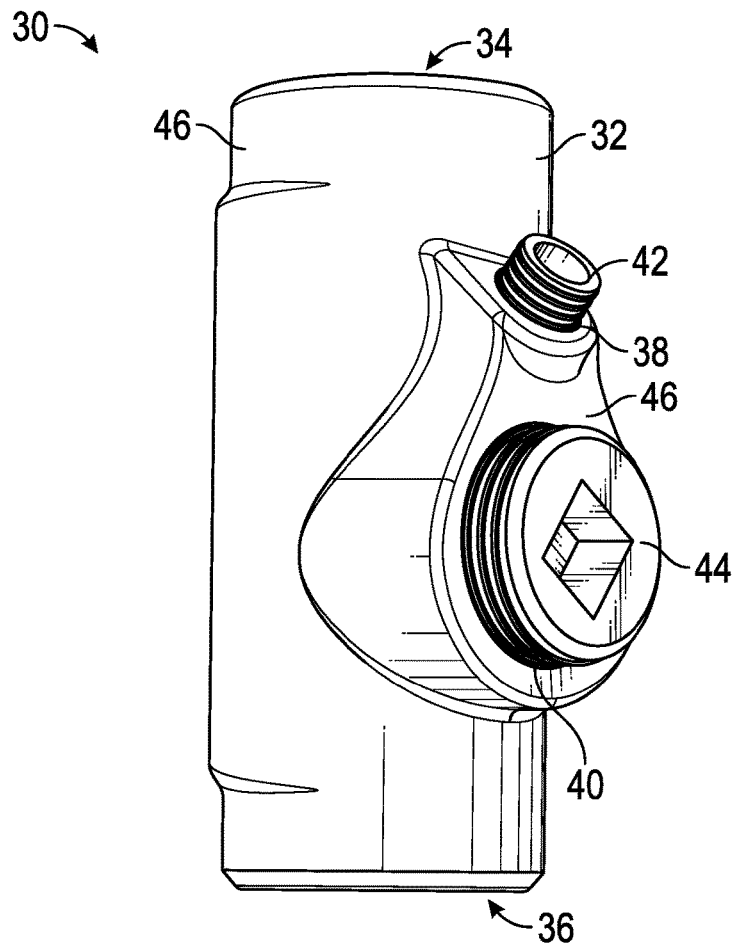
FIG. 2 is an isometric view of a conventional sealing fitting used in Class I hazardous locations.

FIG. 2 is an isometric view of a conventional sealing fitting 30 rated for use in Class I hazardous locations. The sealing fitting 30 includes a wall 32 defining an interior space and having a first end 34 and a second end 36 opposite the first end 34. The sealing fitting 30 includes a first port 38 and a second port 40, each port permitting access to the interior space defined by the wall 32. The first port 38 and the second port 40 are disposed in a port hub 46, the port hub 46 being an outwardly projecting portion of the wall 32. A first plug 42 is removably placed in the first port 38 to selectively open and close the first port 38. A second plug 44 is removably placed in the second port 40 to selectively open and close the second port 40. In the example depicted in FIG. 2, the first and second plugs (42, 44) threadably engage with the first and second ports (38, 40), respectively. The first end 34 and the second end 36 are configured to engage (e.g., threadably) with a conduit to removably couple the sealing fitting 30 to a conduit system in a Class I hazardous location.

Figure 3:
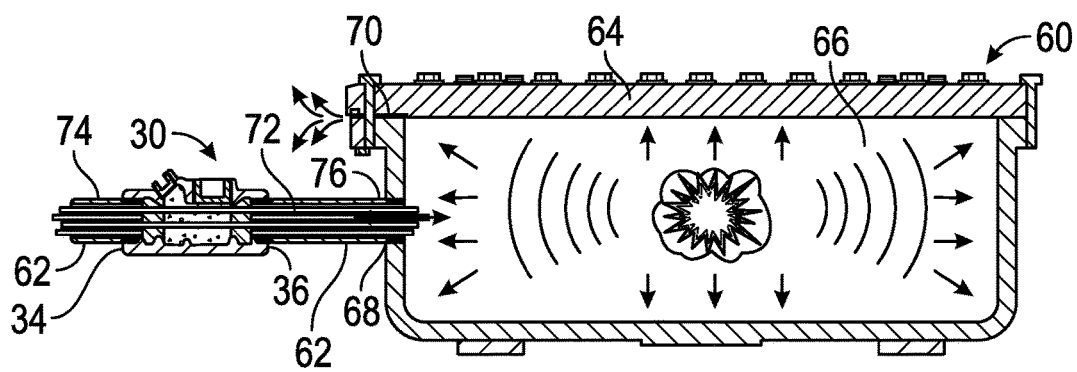
FIG. 3 is a schematic cross-sectional view of an explosion taking place in an example explosion-proof enclosure attached to a conduit system having the example sealing fitting of FIG. 2.

FIG. 3 is a schematic cross-sectional view of an explosion taking place in an example explosion-proof enclosure 60 attached to an example conduit system 62 having the example sealing fitting 30 of FIG. 2. The explosion-proof enclosure 60 includes a container 64 defining an interior space 66. An entrance 68 through the container 64 allows one or more devices housed in the interior space 66 to be connected to the outside world, e.g., via wires or cables 72 carrying, e.g., electricity, electrical signals, or so forth. In this example, the container 64 is equipped with one or more flame paths 70 through which burning gas from an explosion within the container 64 can escape (i.e., vents) and cools before reaching the atmosphere outside the container 64 in a hazardous location, thereby preventing the burning gas from igniting the atmosphere.

The cables/wires 72 pass through the interior of the conduit system 62, through the entrance 68 and into the interior space 66.

The sealing fitting 30 includes the first end 34 and the second end 36 as discussed above. A first conduit 74 of the conduit system 62 connects to the first end 34 of the sealing fitting 30. A second conduit 76 of the conduit system 62 connects on one side with the second end 36 of the sealing fitting 30 and on the opposing side with the entrance 68 to the enclosure 60.

Figure 4:
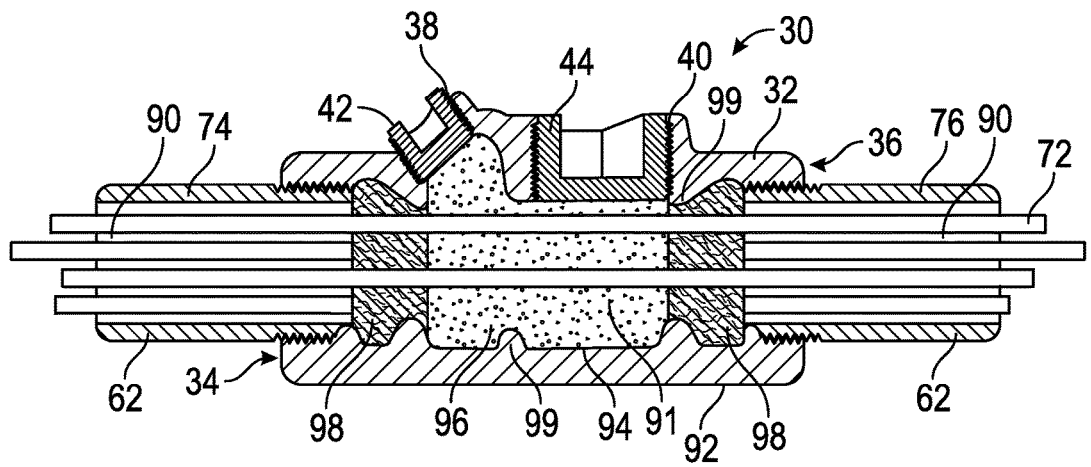
FIG. 4 is a cross-sectional view of the sealing fitting of FIG. 2 connected to two conduits in a horizontal configuration, the sealing fitting including a proper seal.
Figure 5:
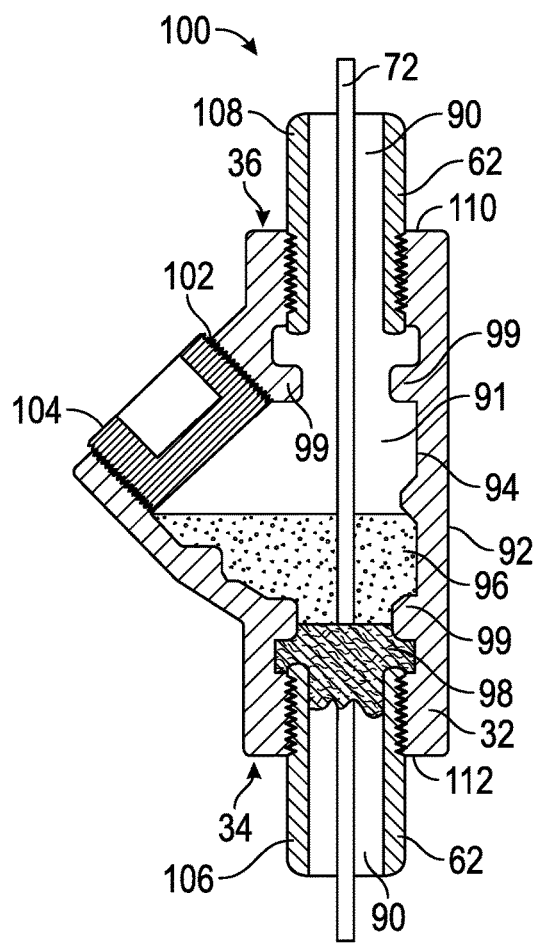
FIG. 5 is a cross-sectional view of a further example of a conventional vertical sealing fitting connected to two conduits.
Figure 6:
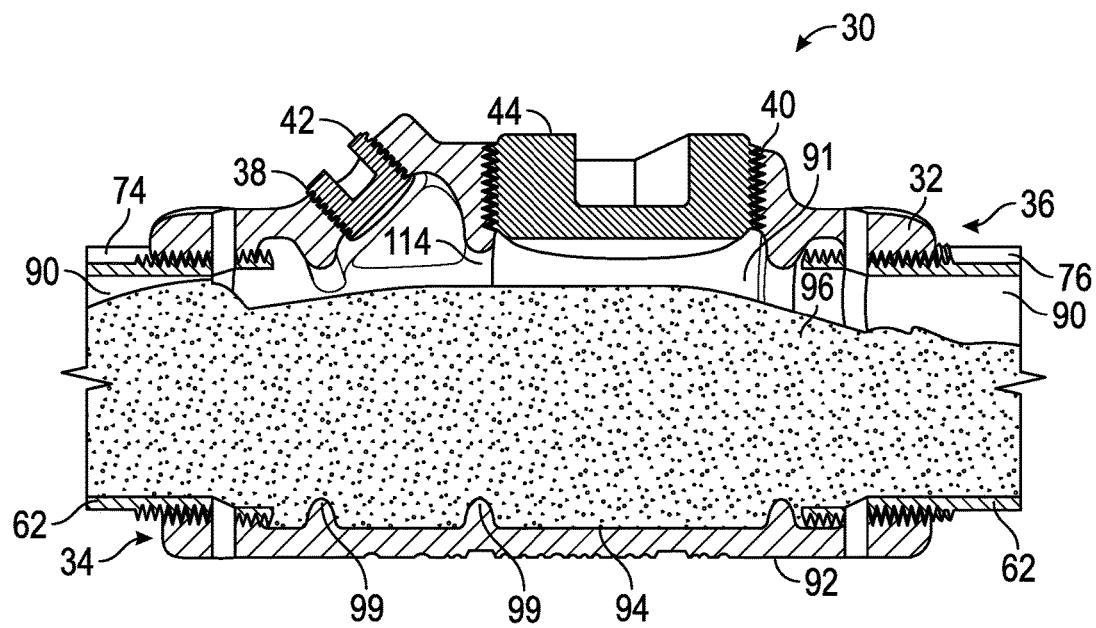
FIG. 6 is a cross-sectional view of the sealing fitting of FIG. 2 connected to two conduits in a horizontal configuration, the sealing fitting including a compromised seal.

FIG. 4 is a cross-sectional view of the sealing fitting 30 of FIG. 2 connected to two conduits in a horizontal configuration, the sealing fitting including a proper seal. FIG. 5 is a cross-sectional view of a further conventional vertical sealing fitting 100 connected to first and second vertical conduits 106 and 108 in a conduit system 62, the first vertical conduit 106 being connected to the first end 34 of the sealing fitting 100 and the second vertical conduit 108 being connected to the second end 36 of the sealing fitting 100. The sealing fitting 100 differs from that of the sealing fitting 30 in that the sealing fitting 100 includes a single port 102 having a single plug 104. The sealing fitting 100 is positioned vertically, such that it has a top 110 and a bottom 112. FIG. 6 is a cross-sectional view of the sealing fitting 30 of FIG. 2 connected to two conduits in a horizontal configuration, the sealing fitting including a compromised seal.

Referring to FIGS. 4-6, the sealing fitting (30, 100) includes the wall 32, the first end 34, the second end 36, the first port (38, 102), the second port 40 (FIGS. 5 and 7), the first plug (42, 104), the second plug 44 (FIGS. 5 and 7), the conduit system 62, the cables/wires 72, the first conduit (74, 106), and the second conduit (76, 108), as discussed above.

In addition, the conduit system 62 includes an interior channel 90 through which the cables/wires 72 pass. The wall 32 of the sealing fitting (30, 100) includes an outer surface 92 and an inner surface 94, the inner surface 94 defining an interior space 91. A sealant 96 fills at least a portion of the interior space 91. One or more sealant dams 98 composed of, e.g. packing fiber, abut the sealant 96 to prevent passage of sealant (e.g., while in a non-solid state) into the conduit system 62. One or more ribs 99 (e.g., annular ribs) protrude from the inner surface 94 into the interior space 91 to aid in securing the sealant and/or the sealant dams 98 in place within the sealing fitting (30, 100). In these examples, the first conduit (74, 106) attaches threadably to the first end 34 of the sealing fitting (30, 100) via a male-female threaded connection. The second conduit (76, 108) attaches threadably to the second end 36 of the sealing fitting (30, 100) via a male-female threaded connection.

Referring to FIG. 4, to create a seal within the interior space 91 of the sealing fitting 30, the conduit system 62 and sealing fitting 30 are connected to each other and to an explosion-proof enclosure. One or both of the first plug 42 and the second plug 44 is removed from the corresponding port (38, 40), e.g., by unscrewing the plug. The cables/wires 72 can then be guided through the interior space 91 from the first conduit 74 to the second conduit 76 (or vice versa) by, e.g., inserting a grasping instrument through one of the ports (38, 40) and grasping the cables/wires 72 to feed them through the sealing fitting 30. Once the cables/wires 72 have been routed through the sealing fitting 30, the sealant dams 98 can be placed in the sealing fitting 30 via the first and/or second ports (38, 40). Once the cables/wires 72 have been fed through the sealing fitting 30 and the sealant dams 98 are in place, sealant 96 can then be poured/placed into one or both of the first port 38 and second port 40 to fill the interior space 91 between the sealant dams 98 around the cables/wires 72 and thereby establish a seal (e.g., upon curing of the sealant 96) that can prevent the passage of potentially igniting gas or other material from the second conduit 76 to the first conduit 74 (or vice versa). After the sealant 96 has been placed, the plugs (42, 44) can be replaced (screwed in) in their respective ports (38, 40).

Seals in hazardous locations should be checked initially after the sealant has cured, and regularly thereafter for damage/degradation that can occur from, e.g., the presence of water in or about the seal, thermal fluctuations, pressure changes and so forth. With the sealing fitting 30 in place within the conduit system 62, the only way to check the integrity of the seal upon its creation or thereafter is by visual inspection through one or both of the first port 38 or the second port 40 upon removal of the corresponding plug (42, 44), and/or prodding of just that portion of the sealant 96 accessible via the ports (38, 40) to check for potential changes in the hardness/consistency of the sealant 96, which could indicate degradation.

The sealant 96 can be selected from one or more of, e.g., cement type sealing compounds, epoxy sealing compounds, polyurethane sealing compounds, and others, and applied initially in liquid form, foam form, putty form, and so forth.

In some examples a channel can be provided through a portion of the sealant 96 in order to drain water that may collect within the sealing fitting 30. Such a channel can lead to one of the ports (38, 40), the sealing fitting oriented such that the port (38, 40) is at least partially facing a vertically downward direction in order to drain off the water through the port.

Referring to FIG. 5, to create a seal within the interior space 91 of the sealing fitting 100, the conduit system 62 and sealing fitting 100 are connected to each other and to an explosion-proof enclosure. The plug 104 is removed from the port 102, e.g. by unscrewing the plug. The cable/wire 72 can then be guided through the interior space 91 from the first conduit 106 to the second conduit 108 (or vice versa) by, e.g., inserting a grasping instrument through the port 102 and grasping the cable/wire 72 to feed it through the sealing fitting 100. The sealant dam 98 can then be placed in the sealing fitting 100 via the port 102. Once the cable/wire 72 has been fed through the sealing fitting 100, sealant 96 can then be poured downward into the port 102. The sealant 96 travels towards the bottom 112 of the sealing fitting 100 under the influence of gravity, settling on the sealant dam 98 and filling up a portion of the interior space 91 around the cable/wire 72 to thereby establish a seal (e.g., upon curing of the sealant 96) that can prevent the passage of a potentially igniting gas or thermal material from the second conduit 108 to the first conduit 106 (or vice versa). After the sealant 96 has been placed, the plug 104 can be replaced in the port 102.

With the sealing fitting 100 in place within the conduit system 62, the only way to check the integrity of the seal upon its creation or thereafter is by visual inspection through the port 102 upon removal of the plug 104, and/or prodding of just that portion of the sealant 96 accessible via the port 102 to check for potential changes in the hardness/consistency of the sealant 96, which could indicate degradation.

Referring to FIG. 6, an improperly formed seal is shown. The sealant 96 has bled into the conduit system 62, leaving a gap 114 in the sealing fitting 30. The gap 114 presents a potentially hazardous condition, in that it could permit the passage of igniting gas or thermal material from an explosion proof enclosure through the sealing fitting 30 and into the conduit system 62 and/or the atmosphere in a hazardous location. The gap 114 may not be detectable through visual inspection or sealant surface prodding via the ports (38, 40). It should be appreciated that FIG. 6 shows just an example of a seal imperfection, and that gaps, cracks and/or other imperfections in the sealant can occur at any location within the sealing fitting 30.

Figure 7:
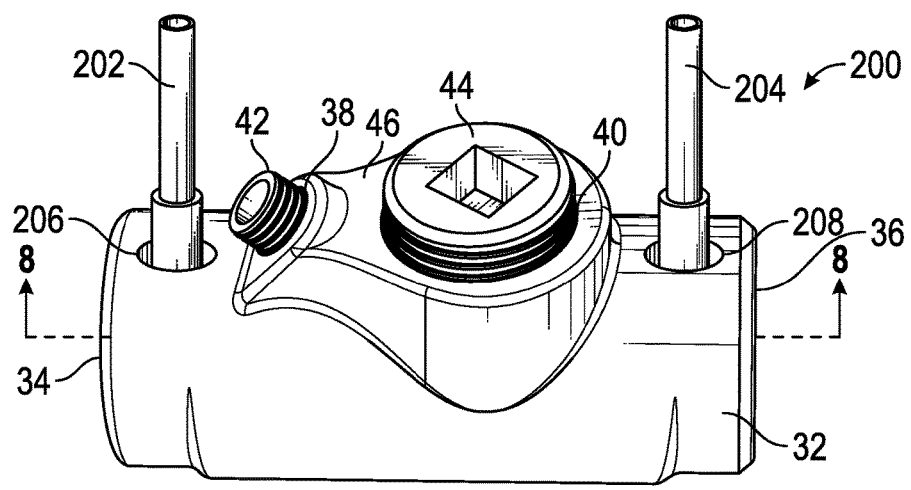
FIG. 7 is an isometric view of an example sealing fitting for use in a Class I hazardous location in accordance with the present disclosure, showing a pair of probes inserted into the sealing fitting.
Figure 8A:
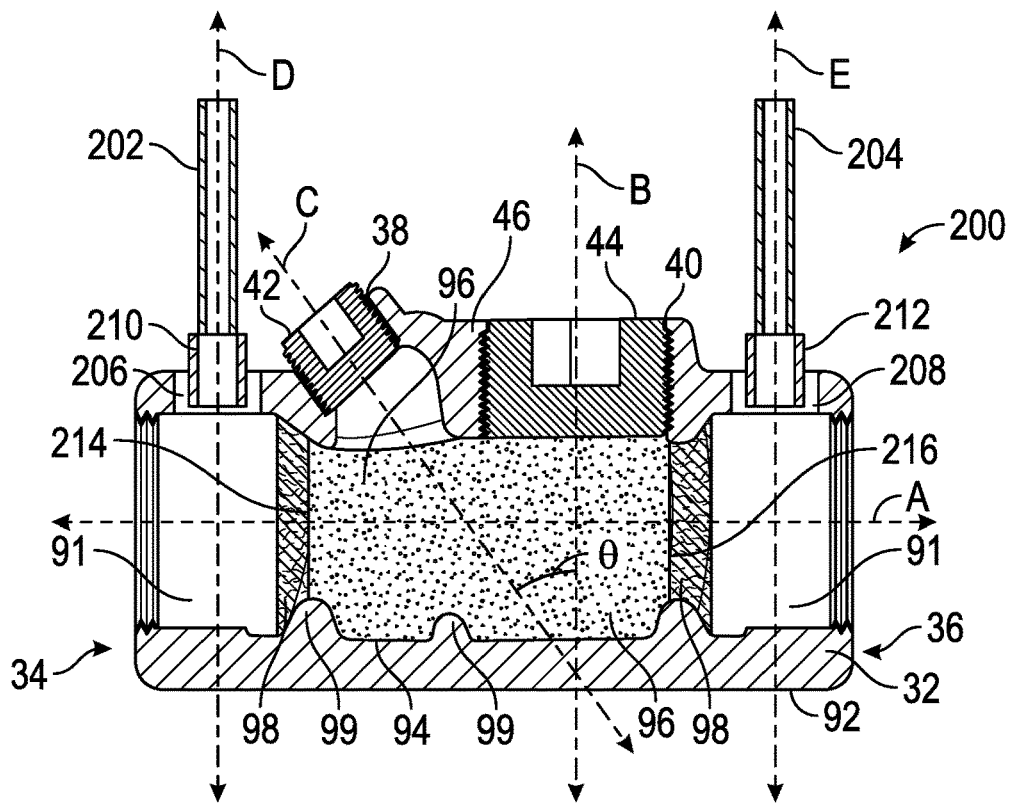
FIG. 8A is a cross-sectional view of the sealing fitting and probes of FIG. 7 along the line marked 8-8 in FIG. 7.
Figure 8B:
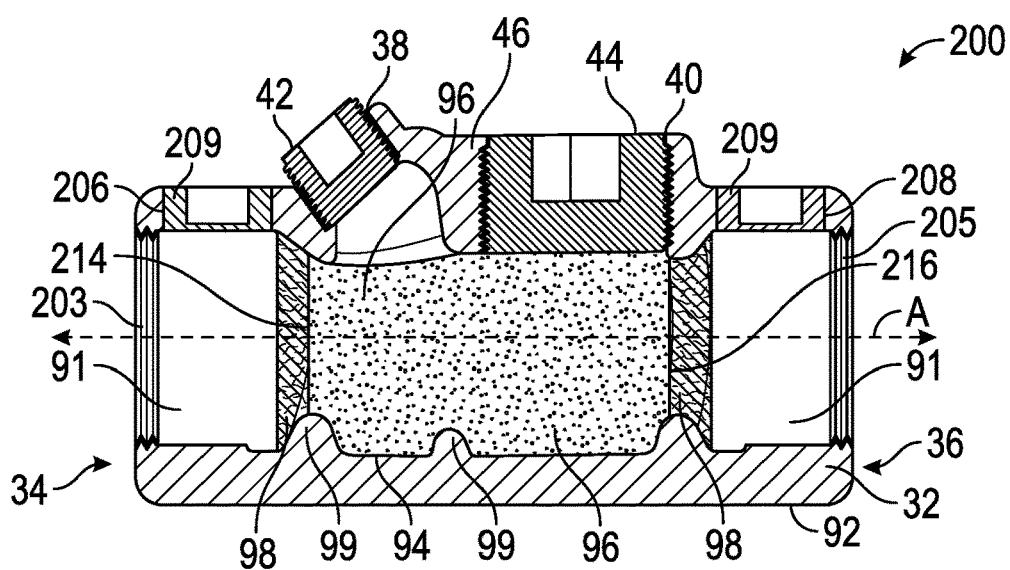
FIG. 8B is the cross-sectional view of the sealing fitting of FIG. 8A without the probes and showing probe ports plugged.

FIG. 7 is an isometric view of an example sealing fitting 200 for use in a Class I hazardous location in accordance with the present disclosure, showing a pair of probes (202, 204) inserted into the sealing fitting 200. FIG. 8A is cross-sectional view of the sealing fitting 200 and probes (202, 204) of FIG. 7 along the line marked 8-8 in FIG. 7. FIG. 8B is the cross-sectional view of the sealing fitting of FIG. 8A without the probes (202, 204), and showing probe ports (206, 208) plugged. FIGS. 8A and 8B shall be referred to collectively as FIG. 8.

Referring to FIGS. 7 and 8, the sealing fitting 200 includes a wall 32 having an outer surface 92 and an inner surface 94, a first end 34, a second end 36, a first port 38, a second port 40, a first plug 42, a second plug 44, an interior space 91, a sealant 96, sealant dams 98 and ribs 99. In addition, in this example, the sealing fitting 200 includes a first probe port 206 and a second probe port 208. The first probe 202 (FIG. 8A) includes a first probe head 210. The second probe 204 (FIG. 8B) includes a second probe head 212. Along the axial direction A the sealant 96 has a distal extreme 214 and a proximal extreme 216.

With reference to FIG. 8A, the second port 40 aligns with an axis B that is perpendicular to the axis A. The first port 38 aligns with an axis C that forms an acute angle θ with the axis B and intersects the axis A obliquely.

With reference to FIG. 8A, each of the first and second probe ports (206, 208) is an aperture through the wall 32 from the outer surface 92 to the inner surface 94. The first probe port 206 is positioned between the first end 34 and the first port 38. The second probe port 208 is positioned between the second end 36 and the second port 40. The first probe port 206 aligns with an axis D that passes through the interior space 91 of the sealing fitting 200 between the screw threads 203 (which are threadably secured to a conduit from the conduit system 62 (FIG. 4)) and the sealant dam 98 that abuts the distal extreme 214 of the sealant 96 and is disposed in a sealant dam receiving portion of the interior space 91 that extends distally from a distal extreme of a sealant receiving portion of the interior space 91. Similarly, the second probe port 208 aligns with an axis E that passes through the interior space 91 of the sealing fitting 200 between the screw threads 205 (which are threadably secured to a conduit from the conduit system 62 (FIG. 4)) and the sealant dam 98 that abuts the proximal extreme 216 of the sealant 96 and is disposed in a sealant dam receiving portion of the interior space 91 that extends proximally from a proximal extreme of a sealant receiving portion of the interior space 91. Thus, when probes (202, 204) are inserted into the probe ports (206, 208), the probe heads (210, 212) are positioned in the interior space 91 between a sealant dam 98 and the end of a conduit (74, 76) that is secured to the screw threads (203, 205) on either side of the sealant 96.

With respect to the radial position of the first probe port 206 and the second probe port 208 about the circumference of the wall 32, any radial position may be selected for each of the first probe port 206 and the second probe port 208.

In some examples, the sealing fitting 200 is elongated in one or both axial directions (i.e., towards the first end 34 and/or the second end 36) on either side of the ports (38, 40) to accommodate the first probe port 206 and/or the second port 208 in the relative positions just described. In some examples, the sealing fitting 200 is not elongated from a standard sealing fitting in order to accommodate the first probe port 206 and/or the second probe port 208.

As discussed, the first probe 202 includes a first probe head 210 and the second probe 204 includes a second probe head 212. The first and second probe ports (206, 208) are sized and configured to receive the probe heads (210, 212), allowing the probe heads (210, 212) to enter the interior space 91 of the sealing fitting 30 on either side of the sealant 96.

With reference to FIG. 8B, in some examples, one or both of the first probe port 206 and the second probe port 208 is pluggable with a plug 209 (e.g., a threaded plug, or a tapered rubber or elastomeric plug for frictionally engaging the port) when the sealant 96 is not being inspected. It should be appreciated that additional probe ports in the wall 32, and additional probes, may be provided beyond what are shown in FIGS. 7-8. Alternatively, the first and second probe ports (206, 208) need not be plugged with the plugs 209, allowing for continuous, real-time measurement of the sealant 96 with probes (202, 204) permanently (or for an extended period of time) inserted in the sealing fitting 200.

In some examples, one of the first and second probes (202, 204) is a signal transmitting probe and the other is a signal receiving probe, the latter being configured to receive one or more signals transmitted by the signal transmitting probe. The signals transmitted between the first and second probes (202, 204) can be selected from a group of signals whose transmission through the sealant 96 is affected by one or more defects in the sealant 96. In some examples, the probes (202, 204) are selected to transmit and receive (via their probe heads (210, 212)), one of, e.g., optical light signals, infrared signals, ultraviolet signals, microwave signals, radar signals, acoustic signals, static or dynamic fluid or vapor pressure signals, ultrasound signals, chemical indicator signals or so forth.

In an example method of inspecting the sealant 96 in FIGS. 7 and 8, plugs are removed from the first probe port 206 and the second probe port 208, while leaving the plugs 42 and 44 in place in their respective ports 38 and 40. A transmitting probe 202 is inserted into the interior space 91 distally from the sealant 96 through the first probe port 206 and between a sealant dam 98 and screw threads 203, and a receiving probe 204 is inserted into the interior space 91 proximally from the sealant 96 through the second probe port 208 between a sealant dam 98 and screw threads 205. One or more signals are transmitted by the transmitting probe 202 through the sealant 96 and received by the receiving probe 204. One or more characteristics of the received signals (e.g., amplitude, frequency, velocity, accompanying noise) is measured and the value compared against one or more predetermined baseline transmission characteristic values for the same signal type through a perfect sealant 96. Based at least in part on the comparison between the measured and baseline values for the characteristic, integrity of the seal in the sealing fitting, and whether or not remedial measures are indicated, are determined.

In some examples, the comparison between the measured and baseline values for the transmitted signal characteristic indicates that the seal is either viable (i.e., verified) or compromised. In some examples, the comparison can provide more precise information about the degree of seal integrity, enabling the technician to track seal degradation over time and predict when a replacement, or other remedial measure, may be required.

FIG. 9 is an isometric view of an assembly 400 in accordance with the present disclosure for inspecting sealant in the sealing fitting 30 of FIG. 2 used in a Class I hazardous location. FIG. 10 is a longitudinal cross-sectional view of the assembly of FIG. 9 along the line marked 10-10 in FIG. 9. Referring to FIGS. 9 and 10, the assembly 400 includes the sealing fitting 30 having the wall 32 defining the interior space 91, the first end 34, the second end 36, the first port 38, the second port 40, the first plug 42, the second plug 44, the conduit system 62 having the interior channel 90, the first conduit 74, the second conduit 76, and the sealant 96 having a distal extreme 214 and proximal extreme 216, as described above. Though not shown, the assembly could alternatively also include one or more of: the cables/wires 72, the sealant dams 98, and the ribs 99, as described above. In addition, in this example the assembly 400 includes one or more signal transmitters 402, and one or more signal receivers 404. The assembly shown in FIGS. 9-10 provides for sealant inspection without requiring the introduction of additional ports (i.e., ports for probes) in the sealing fitting 30 of FIG. 2. That is, the assembly 400 allows testing without accessing the interior of a conduit system or a sealing fitting.

The one or more signal transmitters 402 are positioned on or near the first conduit 74 distally from the distal extreme 214 of the sealant 96. The one or more signal receivers 404 are positioned on or near the second conduit 76 proximally from the proximal extreme 216 of the sealant 96.

In the example assembly 400, an array of four signal transmitters 402 are positioned on the first conduit 74, and a single signal receiver 404 is positioned on the second conduit 76. In some examples an array of two or more signal transmitters/receivers is positioned on one and/or the other of the first and second conduits 74 and 76. In some examples one or more signal transmitters are positioned on the second conduit 76 (i.e., proximally from the proximal extreme 216 of the sealant 96), while one or more signal receivers are positioned on the first conduit 74 (i.e., distally from the distal extreme 214 of the sealant 96).

Referring again to FIGS. 9 and 10, in this example the signal transmitters 402 and the signal receiver 404 are ring-shaped acoustic transducers configured to removably fit around the circumference of the first and second conduits 74 and 76, e.g., by clamping, clipping, fastening or so forth onto the exterior surface (405, 407) of the first and second conduits (74, 76), respectively. The signal transmitters 402 are activated (e.g., by a controller) to emit one or more acoustic pulses 406, portions of which propagate towards the sealant 96. Activation of the signal transmitters 402 can be staggered to provide for constructive interference of the propagating pulse 408 (moving axially through the conduit 74 and the sealing fitting 30 in the direction of the arrows 409) into a higher intensity wave front as it travels toward the sealant 96. The phased growth of the propagating pulse 408 can improve the signal to noise ratio of the signal that is transmitted and detected on the signal receiving side of the sealant 96.

The transmitted pulse 410, having traveled through the sealant 96 (and moving axially through the sealing fitting 30 and the conduit 76 in the direction of the arrows 411) is detected and received by the signal receiver 404. In alternative examples, an array of two or more signal receivers 404 can be alternatively or also provided on or about the second conduit 76 to improve the signal to noise ratio of the signal that is received.

To enhance signal processing, one or more of the signal transmitters 402 and/or the signal receivers 404 can be configured as part of a beamforming system, the one or more signal transmitters 402 and/or signal receivers 404 being configured to execute one or more beamforming algorithms for processing signals transmitted between the one or more signal transmitters 402 and the one or more signal receivers 404.

One or more characteristics of the received signal can be measured and compared against one or more predetermined baseline transmission characteristic values for an acoustic pulse transmitted through a perfect sealant 96. Based at least in part on the comparison between the measured and baseline values for the characteristic, integrity of the seal in the sealing fitting, and whether or not remedial measures are indicated, are determined.

It should be appreciated that, for all embodiments, baseline signal transmission characteristics can be ascertained in any suitable fashion. For example, generic transmission baselines can be generated empirically across multiple sealing fittings and sealants. Alternatively, baselines can be specific to, e.g., a particular fitting and/or sealant and/or usage of the fitting/sealant.

In some examples, the comparison between the measured and baseline values for the transmitted acoustic characteristic indicates that the seal is either viable (i.e., verified) or compromised. In some examples, the comparison can provide more precise information about the degree of seal integrity, enabling the technician to track seal degradation over time and predict when a replacement, or other remedial measure, may be required.

In an example method of inspecting the sealant 96 in FIGS. 9 and 10, the one or more signal transmitters 402 and signal receivers 404 are clamped to the exterior surface 405 of the first conduit 74 and the second conduit 76, the one or more signal transmitters 402 being disposed distally from the distal extreme 214 of the sealant 96; and the one or more signal receivers 404 are clamped to the exterior surface 405 of the second conduit 76, the one or more signal receivers being disposed proximally from the proximal extreme 216 of the sealant 96. The one or more signal transmitters 402 are activated (e.g., by an electronic controller) to provide an acoustic radial wave pulse or a phased growth radial wave pulse that travels axially through the interior channel 90 of the conduit system 62 toward the distal extreme 214 of the sealant 96, through the sealant 96 and into the second conduit 76, where it is received and detected by the one or more signal receivers 404. In some examples, the one or more signal transmitters 402 and/or signal receivers 404 are configured to execute one or more beamforming algorithms for processing signals transmitted between the one or more signal transmitters 402 and the one or more signal receivers 404. One or more characteristics of the received signals (e.g., amplitude, frequency, velocity, accompanying noise) is measured and the value compared against one or more predetermined baseline transmission characteristic values for the same transmitted acoustic signal through a perfect sealant 96. Based at least in part on the comparison between the measured and baseline values for the characteristic, integrity of the seal in the sealing fitting, and whether or not remedial measures are indicated, are determined.

EXAMPLE EMBODIMENTS

Example 1 includes a method for inspecting sealant disposed in a sealing fitting rated for use in a hazardous environment, the sealing fitting comprising a wall defining an interior space and having an inner surface and an outer surface, the method comprising the steps of: providing a first port through the wall into the interior space either proximally from a proximal extreme of a sealant disposed in the sealing fitting or distally from a distal extreme of the sealant; providing a second port though the wall into the interior space the other of proximally from a proximal extreme of the sealant or distally from a distal extreme of the sealant; inserting a probe in each of the first and second ports; receiving a signal sent from the first probe and received by the second probe; and evaluating an integrity of the sealant based on the signal received by the second probe.

Example 2 includes the method of Example 1, wherein the evaluating further comprises comparing a characteristic of the signal received by the second probe to a baseline signal.

Example 3 includes the method of any of Examples 1-2, further comprising a step, prior to the inserting step, of removing first and second plugs disposed in the first and second ports, respectively, and wherein at least one cable passes through the sealant.

Example 4 includes the method of any of Examples 1-3, wherein the sealing fitting further comprises third and fourth ports into the interior space, the third and fourth ports configured for introducing the sealant into the interior space and further configured for visually inspecting the sealant in the interior space.

Example 5 includes the method of any of Examples 1-4, wherein the sealing fitting further comprises a first sealant dam provided in the interior space distally from the distal extreme of the sealant, and a second sealant dam provided in the interior space proximally from the proximal extreme of the sealant.

Example 6 includes the method of any of Examples 1-5, wherein the first probe is configured to transmit, and the second probe is configured to receive, one or more of optical light signals, infrared signals, ultraviolet signals, microwave signals, radar signals, acoustic signals, static or dynamic fluid or vapor pressure signals, ultrasound signals, and chemical signals.

Example 7 includes a method for inspecting sealant disposed in a sealing fitting rated for use in a hazardous environment, the sealing fitting having first and second ends, a sealant disposed in an interior space of the sealing fitting between the first and second ends, and a conduit system comprising a first conduit connected to the first end, and a second conduit connected to the second end, the method comprising: providing a signal transmitter on the first conduit; providing a signal receiver on the second conduit, the signal receiver being configured to receive one or more signals transmitted by the signal transmitter through the sealant; transmitting a signal from the signal transmitter to the signal receiver through the sealant; and evaluating an integrity of the sealant based on the signal received by the signal receiver.

Example 8 includes the method of Example 7, wherein the signal transmitter comprises an array of signal transmitters.

Example 9 includes the method of any of Examples 7-8, wherein the signal receiver comprises an array of signal receivers.

Example 10 includes the method of Example 8, wherein at least one of the signal transmitters is configured to execute at least a portion of a beamforming algorithm.

Example 11 includes the method of Example 10, wherein at least one of the signal receivers is configured to execute at least a portion of a beamforming algorithm.

Example 12 includes the method of Example 7, wherein the signal transmitter comprises an array of signal transmitters and the signal receiver comprises an array of signal receivers.

Example 13 includes the method of any of Examples 7-12, further comprising a step of removably clamping the signal transmitter and the signal receiver to the conduit system.

Example 14 includes the method of any of Examples 7-13, wherein the signal transmitter and the signal receiver are acoustic transducers.

Example 15 includes the method of any of Examples 7-14, wherein the signal transmitter is an array of acoustic transducers configured to provide constructive interference of an acoustic wave front.

Example 16 includes the method of any of Examples 7-15, wherein the evaluating further comprises comparing a characteristic of the signal received by the signal receiver to a baseline signal.

Example 17 includes the method of any of Examples 7-16, wherein the inspecting is performed without accessing the interior space of the sealing fitting and without accessing an interior of the conduit system.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A sealing fitting rated for use in a hazardous environment, the sealing fitting comprising:
    a wall defining an interior space and having an inner surface and an outer surface, and including first and second ports through the wall into the interior space, the ports being disposed, respectively, beyond a proximal extreme and a distal extreme of a sealant disposed within the fitting, the sealant being configured to limit the passage of vapors between an explosion-proof enclosure and the atmosphere in a hazardous location;
    a first probe removably inserted into the first port and configured to transmit one or more signals; and
    a second probe removably inserted into the second port and configured to receive the one or more signals to inspect the integrity of the sealant.

2. The sealing fitting according to claim 1, further comprising first and second plugs removably disposed in the first and second ports, respectively, and wherein at least one cable passes through the sealant.

3. The sealing fitting according to claim 1, further comprising third and fourth ports into the interior space, the third and fourth ports configured for introducing the sealant into the interior space and further configured for visually inspecting the sealant in the interior space.

4. The sealing fitting according to claim 1, further comprising a first sealant dam provided in the interior space distally from the distal extreme of the sealant, and a second sealant dam provided in the interior space proximally from the proximal extreme of the sealant.

5. The sealing fitting according to claim 1, wherein the first probe is configured to transmit, and the second probe is configured to receive, one or more of optical light signals, infrared signals, ultraviolet signals, microwave signals, radar signals, acoustic signals, static or dynamic fluid or vapor pressure signals, ultrasound signals, and chemical indicator signals.

6. The sealing fitting according to claim 1, wherein the sealing fitting is positioned in a hazardous location in which at least one flammable gas or vapor is present in a concentration suitable for igniting.

7. An assembly for inspecting a sealant, comprising:
    a conduit system for use in a hazardous environment, the conduit system comprising a sealing fitting having first and second ends, a sealant disposed in an interior space of the sealing fitting between the first and second ends, and a conduit system comprising a first conduit connected to the first end and defining a conduit axis extending through the conduit and through the first end, and a second conduit connected to the second end;
    a plurality of signal transmitters disposed on the first conduit and serially arranged along the conduit axis; and
    at least one signal receiver disposed on the second conduit, the signal receiver being configured to receive one or more signals transmitted by the plurality of signal transmitters through the sealant.

8. The assembly according to claim 7, comprising at least four of the signal transmitters.

9. The assembly according to claim 7, wherein the at least one signal receiver comprises a plurality of signal receivers.

10. The assembly according to claim 7, wherein the signal transmitters and the at least one signal receiver are removably clamped to the conduit system.

11. The assembly according to claim 7, wherein the signal transmitters and the at least one signal receiver are acoustic transducers.

12. The assembly according to claim 7, wherein the signal transmitters are configured to provide constructive interference of an acoustic wave front.

13. The assembly of claim 7, including exactly two of the signal transmitters.

14. A sealing fitting rated for use in a hazardous environment, the sealing fitting comprising:
    a wall defining an interior space and having an inner surface and an outer surface, the wall being defined by a longitudinal axis, a first end, and a second end, the interior space comprising a sealant receiving portion, a first sealant dam receiving portion, and a second sealant dam receiving portion, the sealant receiving portion having a distal extreme and a proximal extreme, the first sealant dam receiving portion extending distally from the distal extreme of the sealant receiving portion, the second sealant dam receiving portion extending proximally from the proximal extreme of the sealant receiving portion;
    first screw threads at the first end for threadably securing a first conduit to the sealing fitting;
    second screw threads at the second end for threadably securing a second conduit to the sealing fitting;
    a pluggable first port for accessing the interior space, the pluggable first port being disposed in an outwardly projecting portion of the wall and aligned perpendicularly with the longitudinal axis;
    a pluggable second port for accessing the interior space, the pluggable second port being disposed in the outwardly projecting portion of the wall and aligned obliquely with the longitudinal axis;
    a first probe port, the first probe port comprising a first aperture through the wall from the outer surface to the inner surface, the first probe port being positioned between the first end and the pluggable first port and aligning with an axis that passes through the interior space of the sealing fitting between the first screw threads and the first sealant dam receiving portion; and
    a second probe port, the second probe port comprising a second aperture through the wall from the outer surface to the inner surface, the second probe port being positioned between the second end and the pluggable second port and aligning with an axis that passes through the interior space of the sealing fitting between the second screw threads and the second sealant dam receiving portion.

15. The sealing fitting according to claim 14, further comprising a plug removably disposed in each of the pluggable first port and the pluggable second port.

16. The sealing fitting according to claim 14, further comprising a sealant dam provided in each of the first and second sealant dam receiving portions.

17. The sealing fitting according to claim 14, wherein the sealing fitting is positioned in a hazardous location in which at least one flammable gas or vapor is present in a concentration suitable for igniting.

18. A sealing fitting rated for use in a hazardous environment, the sealing fitting comprising:
    a wall defining an interior space and having an inner surface and an outer surface, the wall being defined by a longitudinal axis, a first end, and a second end, the interior space comprising a sealant receiving portion, the sealant receiving portion having a distal extreme and a proximal extreme;

a pluggable first port for accessing the interior space, the pluggable first port being disposed in an outwardly projecting portion of the wall and aligned perpendicularly with the longitudinal axis;

a pluggable second port for accessing the interior space, the pluggable second port being disposed in the outwardly projecting portion of the wall and aligned obliquely with the longitudinal axis;

a first probe port, the first probe port comprising a first aperture through the wall from the outer surface to the inner surface, the first probe port being positioned between the first end and the proximal extreme of the sealant receiving portion and aligning with an axis that passes through the interior space of the sealing fitting; and a second probe port, the second probe port comprising a second aperture through the wall from the outer surface to the inner surface, the second probe port being positioned between the second end and the distal extreme of the sealant receiving portion and aligning with an axis that passes through the interior space of the sealing fitting.

19. The sealing fitting according to claim 18, further comprising a plug removably disposed in each of the pluggable first port and the pluggable second port.

20. The sealing fitting according to claim 18, wherein the sealing fitting is positioned in a hazardous location in which at least one flammable gas or vapor is present in a concentration suitable for igniting.

\* \* \* \* \*